United States Patent [19]

Das et al.

[11] Patent Number: 4,515,972
[45] Date of Patent: May 7, 1985

[54] INTERMEDIATES AND METHOD FOR PRODUCING INTERMEDIATES USEFUL IN THE PREPARATION OF 7-OXABICYCLOHEPTANE PROSTAGLANDIN DERIVATIVES

[75] Inventors: Jagabandhu Das, Plainsboro; Martin F. Haslanger, Lambertville, both of N.J.

[73] Assignee: E. R. Squibb & Sons, Inc., Princeton, N.J.

[21] Appl. No.: 543,564

[22] Filed: Oct. 19, 1983

[51] Int. Cl.³ ................ C07D 493/08; C07D 307/77
[52] U.S. Cl. ........................... 549/229; 549/386/463
[58] Field of Search ..................... 549/229, 386, 463

[56] References Cited

U.S. PATENT DOCUMENTS 4,143,054  3/1979  Sprague ..................... 549/463

*Primary Examiner*—Henry R. Jiles
*Assistant Examiner*—Bernard I. Dentz
*Attorney, Agent, or Firm*—Lawrence S. Levinson; Burton Rodney

[57] ABSTRACT

A method is provided for preparing intermediates for use in preparing 7-oxabicycloheptane prostaglandin derivatives which method includes the steps of reducing (exo)hexa hydro-4,5-epoxyisobenzofuran-1,3-dione to the corresponding diol, subjecting the diol to a chloroformylation reaction to form a compound of the structure

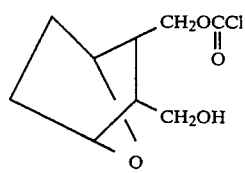

reacting the above with pyridine to form the cyclic carbonate reacting the cyclic carbonate with an alkanol to form the alcohol of the strucure

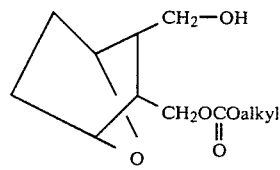

tosylating the above alcohol to form the tosylate and subjecting the above tosylate to a cyanation reaction to form the cyano carbonate of the structure

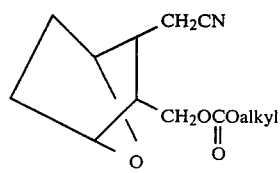

The cyano carbonate may then be reduced by, for example, reaction with diisobutyl aluminum hydride to form the hemiacetal

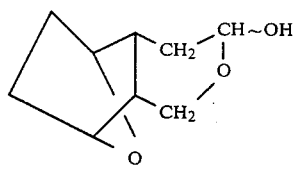

which is used in preparing 7-oxabicycloheptane prostaglandin derivatives as disclosed in U.S. Pat. No. 4,143,054.

New intermediates of the structures set out above, other than the hemiacetal, are also provided.

17 Claims, No Drawings

INTERMEDIATES AND METHOD FOR PRODUCING INTERMEDIATES USEFUL IN THE PREPARATION OF 7-OXABICYCLOHEPTANE PROSTAGLANDIN DERIVATIVES

FIELD OF THE INVENTION

The present invention relates to a method for forming intermediates useful in preparing 7-oxabicycloheptane prostaglandin derivatives.

BACKGROUND OF THE INVENTION

U.S. Pat. No. 4,143,054 to Sprague discloses a method for preparing 7-oxabicycloheptane prostaglandin derivatives wherein maleic anhydride is made to react with an unsubstituted or substituted furan of the formula

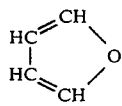    A e.g., in ether solution at room temperature, to form a compound having the formula

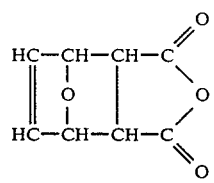    B

Reduction of the compound of formula B, e.g., catalytically, for example, in the presence of palladium-carbon, provides a reduced product having the formula

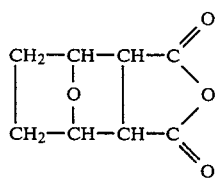    C

The compound of formula C is then converted to a compound having the formula

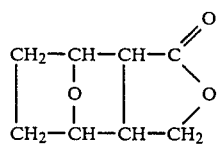    D e.g., by reduction in tetrahydrofuran with a borohydride like sodium borohydride or zinc borohydride.

Treatment of the compound of formula D with diisobutylaluminum hydride or diisobutylborane yields a compound having the formula

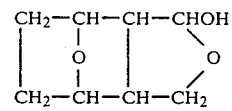    E which then is submitted to Wittig reaction conditions e.g., with an (alkoxymethyl)triphenylphosphonium halide like (methoxymethyl)triphenylphosphonium chloride in the presence of an alkali metal alkylamide like lithium diisopropylamide, a lithium alkyl like n-butyl lithium in an inert organic medium like toluene, tetrahydrofuran or the like, at a temperature in the range of about $-10°$ to $25°$ C.

This reaction produces a compound having the formula

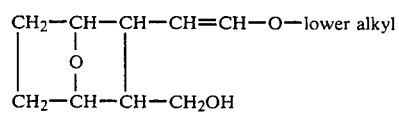    F

The product of formula F is treated with an acid like formic acid or trifluoroacetic acid to yield a product having the formula

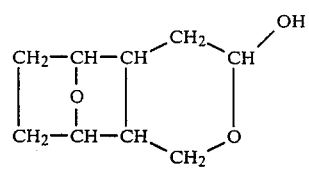    G

The compound of formula G is then used to form 7-oxobicycloheptane or heptene prostaglandin derivatives.

DESCRIPTION OF THE INVENTION

In accordance with the present invention a method is provided for preparing intermediates useful in the preparation of 7-oxabicycloheptane prostaglandin derivatives which method includes the following steps. A dione, having the structure P

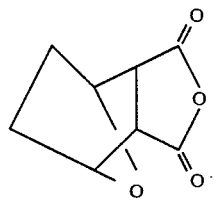    P that is, (exo) or (endo) hexahydro-4,7-epoxyisobenzofuran-1,3-dione, is reduced, for example, by reacting the dione with lithium aluminum hydride or diisobutyl aluminum hydride in the presence of an inert organic solvent such as tetrahydrofuran, ether or toluene at reduced temperatures of from about $-78°$ C. to about $67°$ C. to form a diol Q of the structure

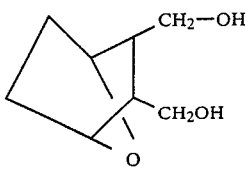

The diol Q is subjected to a chloroformylation reaction by reacting Q dissolved in an inert organic solvent as described above, with phosgene in the presence of an aromatic solvent such as toluene, benzene or xylenes, to form an alcohol of the structure

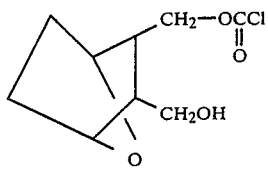

(which is a novel compound).

The alcohol I is dissolved in an inert organic solvent such as methylene chloride, tetrahydrofuran or ether and then reacted with an organic base, such as pyridine, triethylamine, N,N-dimethylaminopyridine or diazabicycloundecane (DBU) at reduced temperatures of from about −78° C. to about 25° C., to form cyclic carbonate II (which itself is a novel compound)

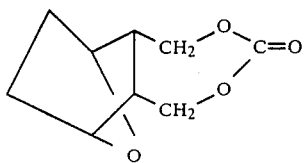

The cyclic carbonate II is then subjected to alcoholysis by reacting II with an alkanol (alkyl-OH) having from 1 to 12 carbons, such as ethanol, n-propanol, isopropanol, butanol, pentanol, hexanol, heptanol, octanol, nonenol or decanol, including all the various isomers thereof, preferably isopropyl alcohol, employing a molar ratio of II:alkanol of within the range of from about 1:10 to about 1:100 to form hydroxycarbonate III (which itself is a novel compound)

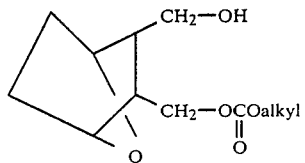

(wherein alkyl contains 1 to 12 carbons as defined hereinafter).

Thereafter, the hydroxy carbonate III is then tosylated (or otherwise protected) by reacting III (dissolved in methylene chloride, and a basic solvent such as pyridine, triethylamine or dimethylaminopyridine) with tosyl chloride or other protecting agent, such as methane sulfonyl chloride (mesyl chloride) and trifluoromethanesulfonic anhydride, to form the tosylate IV or other protected compound (which itself is a new compound)

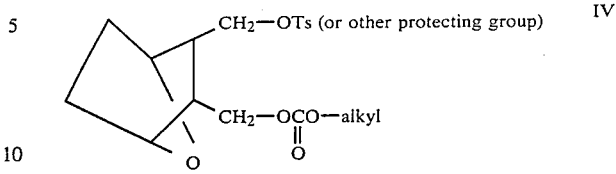

Then, the tosylate IV dissolved in an inert solvent such as dimethylsulfoxide, or dimethylformamide is cyanated by reacting IV with an alkali metal cyanide such as NaCN or KCN employing a molar ratio of IV:cyanide of within the range of from about 1:1 to about 10:1, at elevated temperatures of from about 80° C. to about 130° C., in an inert atmosphere, such as an argon atmosphere, to form the cyanocarbonate V (which itself is a new compound)

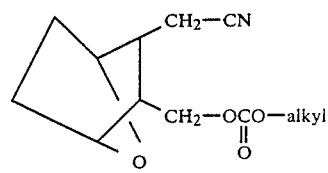

Thereafter, the cyanocarbonate V may be reduced, for example, by reacting V with diisobutyl aluminum hydride, in the presence of toluene or other inert organic solvent such as tetrahydrofuran, methylene chloride or ether, at reduced temperatures of from about −78° C. to about 0° C. to form hemiacetal R of the structure

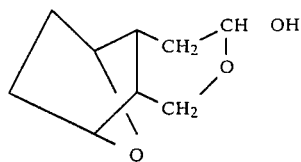

(the wavy line indicates that the hydroxyl group may be either trans or cis to the ring)

The hemiacetal R, also referred to as (exo) or (endo) octahydro-5,8-epoxy-1H-benzopyran-3-ol may be employed to prepare various 7-oxabicycloheptane prostaglandin derivatives as described in U.S. Pat. No. 4,143,054 to Sprague.

In addition, in accordance with the present invention, new intermediates for use in preparing 7-oxabicycloheptane prostaglandin derivatives are provided having the general structure

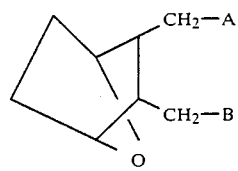

wherein A is

OH. O-Protecting group (such as O-tosyl, O-mesyl or O-trifluoromethanesulfonyl) or CN and B is OH wherein A is

and B is

where A is OH, O-Protecting group (such as O-tosyl, O-mesyl, or O-trifluoromethane sulfonyl) or CN.

Thus, the new compounds of the invention as covered by formula VI have the following structures

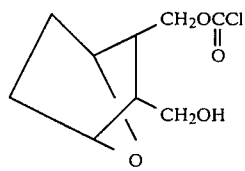   I

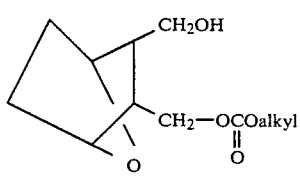   III (where alkyl is preferably isopropyl)

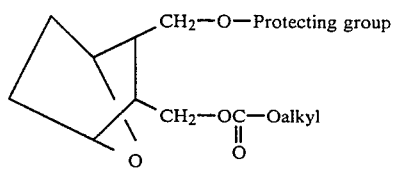   IV (wherein alkyl is preferably isopropyl)

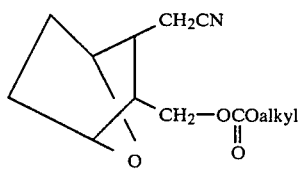   V (wherein alkyl is preferably isopropyl)

Another new intermediate in accordance with the present invention and prepared as described above has the structure

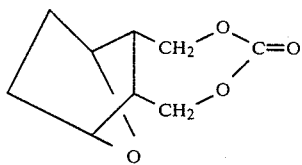   II

The various formulae depicting the new intermediates of the invention include all stereoisomers of such intermediates.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an arylalkyl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The nucleus in each of the compounds of the invention is depicted as

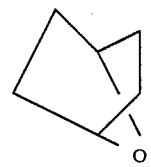

for matter of convenience; it will also be appreciated that the nucleus in the compounds of the invention may be depicted as

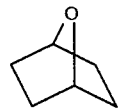

The compounds of this invention are useful as intermediates for preparing 2-oxabicycloheptane prostaglandin derivatives as described in U.S. Pat. No. 4,143,054. These prostaglandins are useful as cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The following Example represents a preferred embodiment of the present invention. All temperatures are expressed in degrees Centigrade unless indicated otherwise.

EXAMPLE (Exo)Octahydro-5,8-epoxy-1H-benzopyran-3-ol

A. (1α,2β,3β,4α)-cis-exo-7-oxabicyclo[2.2.1]heptane 2,3-dimethanol

To a suspension of 11.4 g lithium aluminum hydride (300 mmole, 1.6 eq) in 400 ml of dry THF at 0° C. was added dropwise a solution of 32 g of (exo)hexahydro-4,7-epoxyisobenzofuran-1,3-dione (cis-exo-aldehyde), prepared as described in Example 1 of U.S. Pat. No. 4,143,054, (190 mmol) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. (1α,2β,3β,4α)-cis-exo-2-hydroxymethyl-3-chlorooxycarbonyloxymethyl-7-oxabicyclo[2.2.1]heptane and C. (1α,2β,3β,4α)-cis-exo-7-oxabicyclo-[2.2.1]heptane 2,3-dimethanol carbonate To a solution of 10 g title A diol (63.2 mmole) in 40 ml dry THF at 0° C. was added with stirring 55 ml of a 12.5% by weight solution of phosgene in toluene (63.2 mmole, 1 eq.) dropwise over a period of 30 minutes. Argon was then bubbled through the reaction mixture for 15 minutes. The mixture was concentrated to give title B compound in the form of a crude oil.

The title B oil was dissolved in 30 ml of dry $CH_2Cl_2$ and cooled to −50° C. To this solution was added dropwise a solution of 10 ml pyridine in 10 ml $CH_2Cl_2$. The mixture was stirred for 10 minutes and quenched with $H_2O$. The mixture was then extracted thoroughly with $CH_2Cl_2$. The organic extract was dried over $MgSO_4$ and concentrated to give the title C cyclic carbonate as a crystalline solid (10.7 g).

D. (1α,2β,3β,4α)-cis-exo-2-hydroxymethyl-3-isopropyloxycarbonyloxymethyl-7-oxabicyclo[2.2.1]heptane A mixture of 10.7 g title C cyclic carbonate (58.1 mmole) in 100 ml isopropanol was refluxed for 24 hours. Excess isopropanol was removed under reduced pressure to give 14.4 g title D hydroxycarbonate as a viscous oil.

E. (1α,2β,3β,4α)-cis-exo-2-p-toluenesulfonyloxymethyl-3-isopropyloxycarbonyloxymethyl-7-oxabicyclo[2.2.1]heptane To a solution of 19.7 g title D hydroxy carbonate (80 mmole) in 30 ml $CH_2Cl_2$ and 12.8 ml pyridine (160 mmole, 2 eq.) was added 18.5 g p-toluenesulfonyl chloride (96 mmole, 1.2 eq.). The mixture was stirred at 25° C. for 36 hours, then diluted with 200 ml ether, and washed with 100 ml. The organic layer was dried over $MgSO_4$ and concentrated to give 32.8 g of crude title E tosylate.

F. (1α,2β,3β,4α)-cis-exo-2-cyanomethyl-3-isopropyloxycarbonyloxymethyl-7-oxabicyclo[2.2.1]heptane To a solution of 24.0 g title E crude tosylate (60 mmole) in 20 ml DMSO was added with stirring 6.0 g powdered sodium cyanide (120 mmole, 2 eq.). The mixture was heated at 90°–95° C. for 1.5 hours under an argon atmosphere. The cooled mixture was diluted with 50 ml water and extracted with five 100 ml portions of ether. The ethereal extracts were dried over anhydrous $MgSO_4$ and filtered through a bed of florosil. The filtrate was concentrated, and the residue was recrystallized with ether/hexanes to give 8.4 g title F cyanocarbonate as a light yellow crystalline solid.

G. (Exo)Octahydro-5,8-epoxy-1H-benzopyran-3-ol

To a solution of 4.43 g of title F cyanocarbonate (17.51 mmole) in 20 ml of dry toluene at −78° C. was added dropwise 60 ml of a 25% by weight solution of diisobutylaluminum hydride in toluene (105 mmole, 2 eq.). After stirring at −78° C. for 4 hours the reaction was quenched with a saturated ammonium chloride solution. The mixture was warmed to 25° C. and 50 ml of a 1N aqueous hydrochloric acid solution was added. The organic layer was separated and the aqueous layer was saturated with sodium chloride and extracted several times with methylene chloride. The combined organic extract was dried over anhydrous $MgSO_4$ and concentrated to give 2.98 g of crude title G hemiacetal.

The title G hemi-acetal may be employed as described in U.S. Pat. No. 4,143,054 to Sprague to prepare 7-oxabicycloheptane prostaglandin derivatives.

What is claimed is:

1. A method for preparing a hemiacetal of the structure

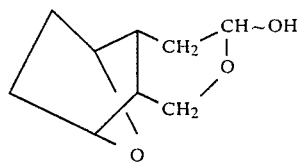

which comprises reducing a dione (mesoanhydride) of the structure

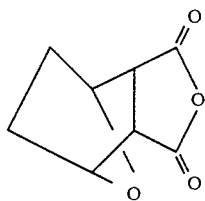

to form a diol of the structure

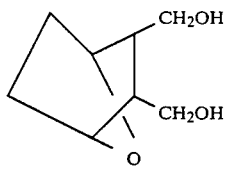

chloroformylating the diol by reacting same with phosgene to form the alcohol of the structure

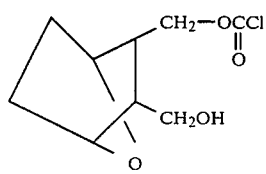

reacting the alcohol with pyridine to form the cyclic carbonate of the structure

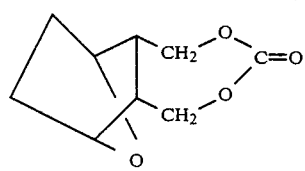

reacting the cyclic carbonate with an alkanol to form an alcohol of the structure

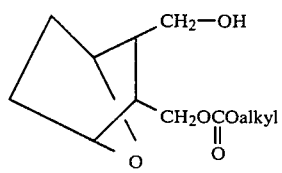

reacting the alcohol with a protecting compound containing a sulfonyl group to form the protected alcohol of the structure

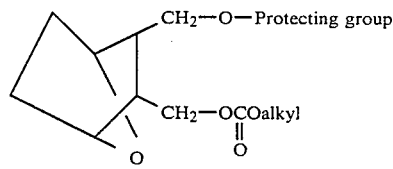

wherein "Protecting group" contains a sulfonyl moiety, reacting the protected alcohol with a cyanide to form the cyanocarbonate of the structure

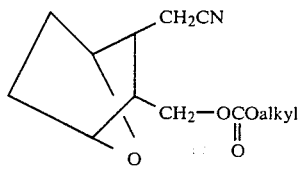

and reducing the cyano carbonate to form the hemiacetal.

2. The method as defined in claim 1 wherein the mesoanhydride is reduced by reacting same with lithium aluminum hydride, diisobutylaluminum hydride or diborane.

3. The method as defined in claim 1 wherein said alkanol contains 1 to 12 carbons.

4. The method as defined in claim 3 wherein said alkanol is isopropanol.

5. The method as defined in claim 1 wherein said protecting group is tosyl, mesyl or trifluoromethane sulfonyl.

6. The method as defined in claim 1 wherein said cyanide is an alkali metal cycanide.

7. The method as defined in claim 6 wherein said alkali metal cyanide is sodium cyanide or potassium cyanide.

8. The method as defined in claim 1 wherein the cyanocarbonate is reduced by reaction with diisobutyl aluminum hydride to form the hemiacetal.

9. An intermediate for use in preparing 7-oxabicycloheptane prostaglandin derivatives, said intermediate having the structure

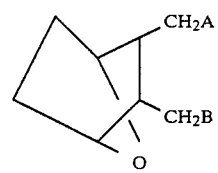

wherein
A is

OH, O-Protecting group, or CN and
B is OH where A is

and B is

wherein A is OH, O-Protecting group or CN and wherein "Protecting group" contains a sulfonyl moiety.

10. The intermediate as defined in claim 9 having the structure

11

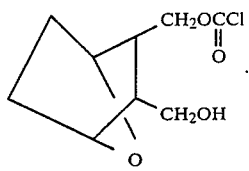

11. The intermediate as defined in claim 9 having the structure

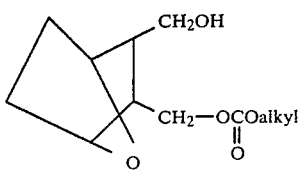

12. The intermediate as defined in claim 11 where alkyl is isopropyl.

13. The intermediate as defined in claim 9 having the structure

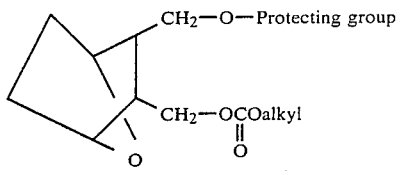

wherein "Protecting group" contains a sulfonyl moiety.

14. The intermediate as defined in claim 13 wherein the protecting group is tosyl or mesyl.

15. The intermediate as defined in claim 9 having the structure

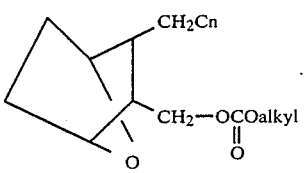

16. The intermediate as defined in claim 15 wherein alkyl is isopropyl.

17. An intermediate for use in preparing 7-oxabicycloheptane prostaglandin derivatives, said intermediate having the structure

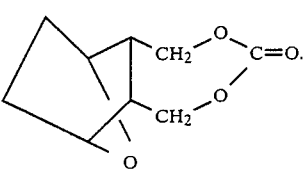

* * * * *

UNITED STATES PATENT AND TRADEMARK OFFICE
CERTIFICATE OF CORRECTION

PATENT NO. : 4,515,972                                   Page 1 of 2

DATED : May 7, 1985

INVENTOR(S) : Jagabandhu Das et al.

It is certified that error appears in the above—identified patent and that said Letters Patent is hereby corrected as shown below:

On the abstract page, column 2, first line, after "carbonate" first occurrence, insert --of the structure

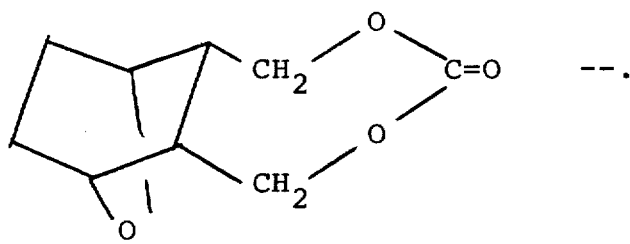 --.

On the abstract page, column 2, first line of the second paragraph, after "tosylate" insert the structure -- 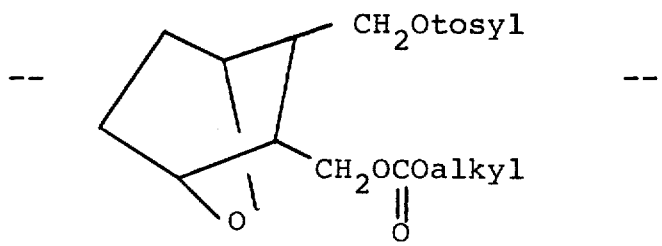 --

UNITED STATES PATENT AND TRADEMARK OFFICE
CERTIFICATE OF CORRECTION

PATENT NO. : 4,515,972
DATED : May 7, 1985
INVENTOR(S) : Jagabandhu Das et al.

It is certified that error appears in the above—identified patent and that said Letters Patent is hereby corrected as shown below:

Column 4, structure R should read

-- 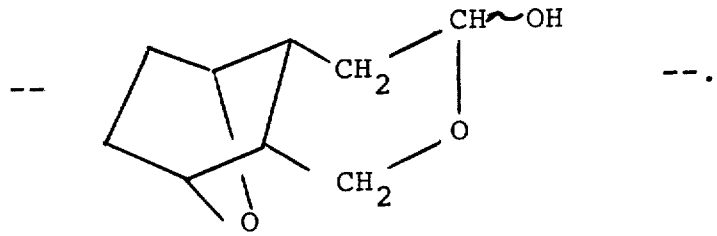 --.

Column 12, claim 15, in the structure "$CH_2Cn$" should read --$CH_2CN$--.

Signed and Sealed this

Twenty-second Day of October 1985

[SEAL]

Attest:

DONALD J. QUIGG

Attesting Officer

Commissioner of Patents and
Trademarks—Designate